US00PP09905P

United States Patent [19]

Kent

[11] Patent Number: Plant 9,905

[45] Date of Patent: May 27, 1997

[54] BROMELIAD PLANT NAMED 'AECHMEA 212'

[75] Inventor: Jeffrey C. Kent, Vista, Calif.

[73] Assignee: Kent's Bromeliad Nursery, Inc., Vista, Calif.

[21] Appl. No.: 563,012

[22] Filed: Nov. 27, 1995

[51] Int. Cl.[6] ..... A01H 5/00

[52] U.S. Cl. ..... Plt./88.8

[58] Field of Search ..... Plt./88.8

*Primary Examiner*—Howard J. Locker

*Attorney, Agent, or Firm*—Frank B. Robb; John H. Vynalek

[57] ABSTRACT

A cross of *Aechmea cucculata* 'White' and *Aechmea fasciata* 'Spineless' (both unpatented) which differs from other crosses of the same in the fact that it is spineless and has glaucous, silvery leaves and an upright growth setting off a vivid pink inflorescence.

1 Drawing Sheet

This present invention relates to Bromeliads and, primarily, to a bromeliad which is the product of crossing a seed parent *Aechmea cucculata* 'White' (unpatented) with the pollen parent *Aechmea fasciata* 'Spineless', likewise unpatented.

In point of fact, the plant is the product of a long period of development which I have conducted over many years in the effort to provide plants of the Bromeliad family which are commercially desirable and healthy as far as being able to ship and display.

As a result of this program, I have developed the instant variety and selected the same from a cultivated area in a large planting of Aechmea as indicated herein and this particular plant, I denominate 'Aechmea 212'.

I have caused the plant to be reproduced by tissue culture in the neighborhood of Ranch Santo Fe, Calif. and found that over time as a result of such asexual reproduction and continuing reproduction the plant holds true from generation to generation.

The seed parent, *A. cucculata* 'White', is heavily spined having long white bracts and an upright growth habit. The pollen parent, *A. fasciata* 'Spineless', on the other hand, is spineless resulting in a spineless Aechmea hybrid which is unusual for this genus and more desirable from the consumers' point of view.

The inflorescence of this Aechmea hybrid more resembles the pollen parent in general conformation, except that the floral branches are longer and more openly spaced. The bracts are darker and brighter color (40-4) than the pollen parent's (39-3).

Generally speaking, this hybrid of *A. cucculata*×*A. fasciata* is distinguished from other plants resulting from crosses from different members of the parental species by expressing an attractive glaucous, silvery leaves and upright growth habit which sets off the vivid pink of the inflorescence. This hybrid is some what larger than either parent and holds its color well in dim light indoors for two to three months.

BRIEF DESCRIPTION OF THE DRAWING

I append hereto a color illustration of a typical plant of my new variety and is shown as near the actual colors of the plant as photo reproduction of this kind can depict.

Color values presented in this disclosure were taken from the Munsell Color Cascade. Color definitions of ordinary meaning are presented where appropriate and properly descriptive. Colors are approximate as color depends on horticultural practices such as light level and fertilization rate, among others, without, however any variance in genotype.

In order to point out more specifically the most notable aspects and novel characteristics of the plant of this invention, as set forth above, the following detailed botanical description presents the general and the specific characteristics of 'Aechmea 212'.

General characteristics:

*Type.*—Monocot, perennial.

*Habit.*—Large, medium, upright with older leaves drooping and dense.

*Hardiness.*—Tender.

*Size.*—About 24 to 26 inches in width and about 20 to 23 inches, including inflorescence, in height.

*Shape.*—Vase formed.

Leaves:

*Length.*—22 inches.

*Width.*—3 inches. Large to medium size, acuminate, abruptly pointed, medium thickness, light green and smooth.

*Color.*—20-10, glaucous on obverse and reverse, more dense on reverse.

*Margin.*—Smooth.

Inflorescence: Branched.

Flower buds: Tender, medium, pointed and appressed.

Bracts:

*Primary bracts.*—Acuminate with the lower primary bracts ascending; Size of bracts beginning about 5 inches×1¼ inches decreasing in size to 2¾ inches×¾ inches: Color 40-4.

*Floral bractlets.*—Clasping each flower and terminal branches; Color 40-4.

Flowers: Cylindrical corolla; Color 26-2 at anthesis; Petals half open at anthesis.

It is claimed:

1. A new and distinct cultivar of Aechmea plant substantially as herein described and illustrated, characterized particularly as to novelty by its glaucous, silvery leaves and an upright growth habit setting off a vivid pink inflorescence.

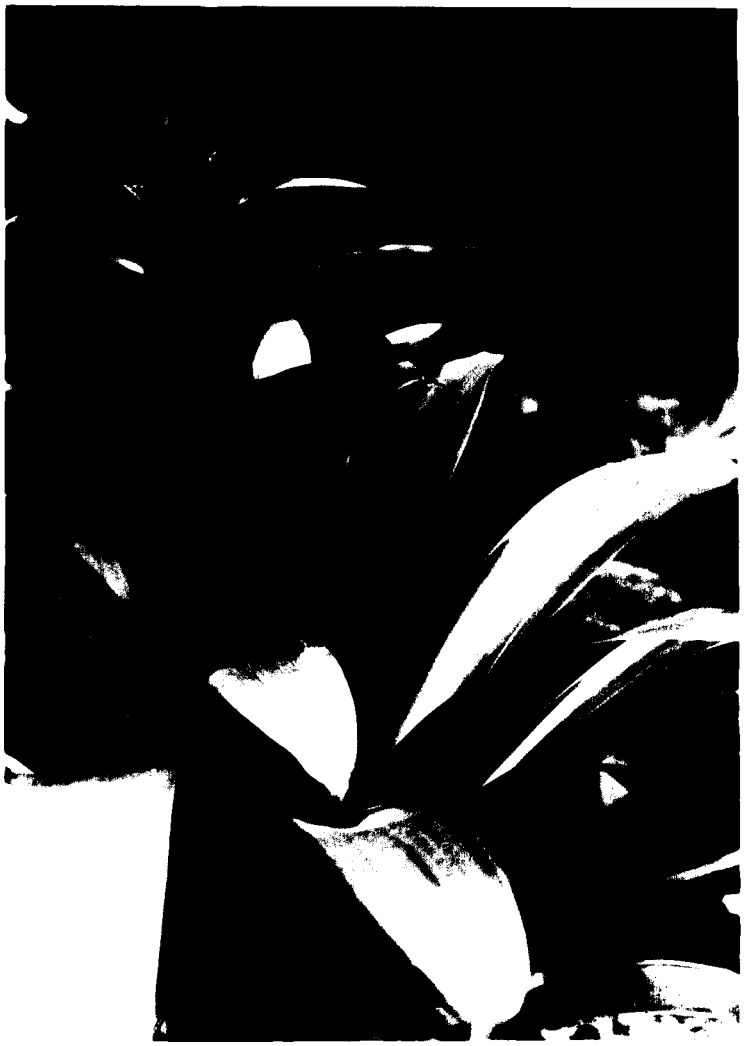

* * * * *